(12) United States Patent
Kodden et al.

(10) Patent No.: US 7,726,233 B2
(45) Date of Patent: Jun. 1, 2010

(54) BREWING RECEPTACLE AND A FOAM UNIT AND A BEVERAGE MAKER COMPRISING SUCH A BREWING RECEPTACLE

(75) Inventors: Hans Kodden, Hoogeveen (NL); Ben Arlett, Cambridge (GB); Christopher James Smith, Cambridgeshire (GB); James Neave, Cambridgeshire (GB); David Stuart Harris, Cambridgeshire (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 884 days.

(21) Appl. No.: 10/557,682

(22) PCT Filed: May 18, 2004

(86) PCT No.: PCT/IB2004/050729
§ 371 (c)(1),
(2), (4) Date: Nov. 22, 2005

(87) PCT Pub. No.: WO2005/051180
PCT Pub. Date: Jun. 9, 2005

(65) Prior Publication Data
US 2007/0039476 A1    Feb. 22, 2007

(30) Foreign Application Priority Data
May 27, 2003  (EP)  .................................. 03253319

(51) Int. Cl.
*A47J 31/00* (2006.01)
(52) U.S. Cl. .............................. 99/284; 99/323; 99/295
(58) Field of Classification Search .................. 99/323, 99/295, 284, 302 R, 306, 304, 307
See application file for complete search history.

(56) References Cited

U.S. PATENT DOCUMENTS

| 4,149,454 | A  | * | 4/1979 | Kemp ........................... 99/295 |
| 6,192,786 | B1 |   | 2/2001 | Gasser et al. |
| 7,093,530 | B2 | * | 8/2006 | Meister et al. ................ 99/295 |

FOREIGN PATENT DOCUMENTS

EP    1101430 A1    5/2001

* cited by examiner

*Primary Examiner*—Reginald L Alexander

(57) ABSTRACT

A brewing receptacle for an apparatus for brewing a beverage such as coffee. The receptacle has a brewing chamber (13; 63; 113) having an entry passage and an exit passage for displacing water through the chamber (13; 63; 113) for brewing the beverage, a bottom (14; 64; 114) for supporting the particles (18; 118, 118') (18), and a discharge 5 opening (19; 69; 119) in the bottom (14; 64; 114) for discharging beverage liquid through the bottom (14; 64; 114). At least the bottom (14; 64; 114) is invertible between a first and a second operative position. The brewing chamber (13; 63; 113) has a first volume and a first shape when the bottom (14; 64; 114) is in said first position and at least a second volume or a second shape of the brewing chamber in said second position is different from the first volume or shape, respectively.

9 Claims, 5 Drawing Sheets

BREWING RECEPTACLE AND A FOAM UNIT AND A BEVERAGE MAKER COMPRISING SUCH A BREWING RECEPTACLE

The invention relates to a brewing receptacle, to a foam unit, and to a beverage maker comprising such a brewing receptacle, comprising at least one brewing chamber operative for holding particles, the at least one chamber having at least one entry passage and an exit passage for displacing water through the chamber for brewing a beverage and having a bottom for supporting the particles and a discharge opening in the bottom for discharging beverage liquid through the bottom, characterized in that at least the bottom is invertible between a first and a second operative position, an in that the at least one brewing chamber has a first volume and a first shape when in the first position and has a second volume and a second shape when in the second position, at least one of the second volume and shape being different from the first volume and shape.

A brewing receptacle of the above type is known from U.S. Pat. No. 6,192,786. A lateral wall of the coffee receptacle and a bottom formed by a filter plate define the volume of the brewing chamber of the receptacle, so that portioning is substantially predetermined. According to this document, the receptacle is intended for receiving ground coffee. For adapting the volume of the brewing chamber to different amounts of coffee granulate from which coffee is to be brewed, the filter plate is arranged such that it is displaceable stepwise relative to the lateral wall of the coffee receptacle into predetermined positions in axial direction of the coffee receptacle, each position resulting in a different internal height of the brewing chamber. To this end, an elevating means in the form of a cam element is rotatably arranged in the coffee receptacle and supports projections of the filter plate in circumferentially distributed positions. A rotational movement of the cam element is capable of adjusting the position in which the filter plate is held by the cam element. The cam element is arranged in the coffee receptacle. With the volume of the brewing chamber, also the shape of the brewing chamber is changed, since the depth is reduced while the diameter remains the same.

A problem of such a coffee receptacle is that the rotatable cam element in the coffee receptacle forms an additional element, and that the structure designed to operate the cam element inside the coffee receptacle is relatively complicated and therefore costly.

It is an object of the present invention to provide a simpler solution that allows to change the volume and/or the shape of the brewing chamber in which particles from which a beverage is to be brewed are accommodated in a configuration of a particular shape.

According to the present invention, this object is achieved by providing a brewing receptacle as previously described. Furthermore, according to the invention, this object can be achieved by providing a set of parts, a foam unit or a beverage maker which each comprise such a brewing receptacle.

Since the change in total volume, shape, or both volume and shape of the operational brewing chamber or chambers is achieved by inverting at least the bottom of the brewing chamber or chambers, no additional support member is required for changing the overall volume of the operational brewing chamber or brewing chambers. Furthermore, changing the total volume, shape, or both volume and shape of the brewing chamber or chambers that are operational for brewing is easy, also in the absence of a complicated operating structure, because it is sufficient to provide that the bottom of the brewing chamber or chambers is arranged in the proper orientation.

Particularly advantageous embodiments of the invention are set forth in the dependent claims.

Further features, effects and details of the invention are described with reference to the embodiments shown in the drawings.

Figure 1:
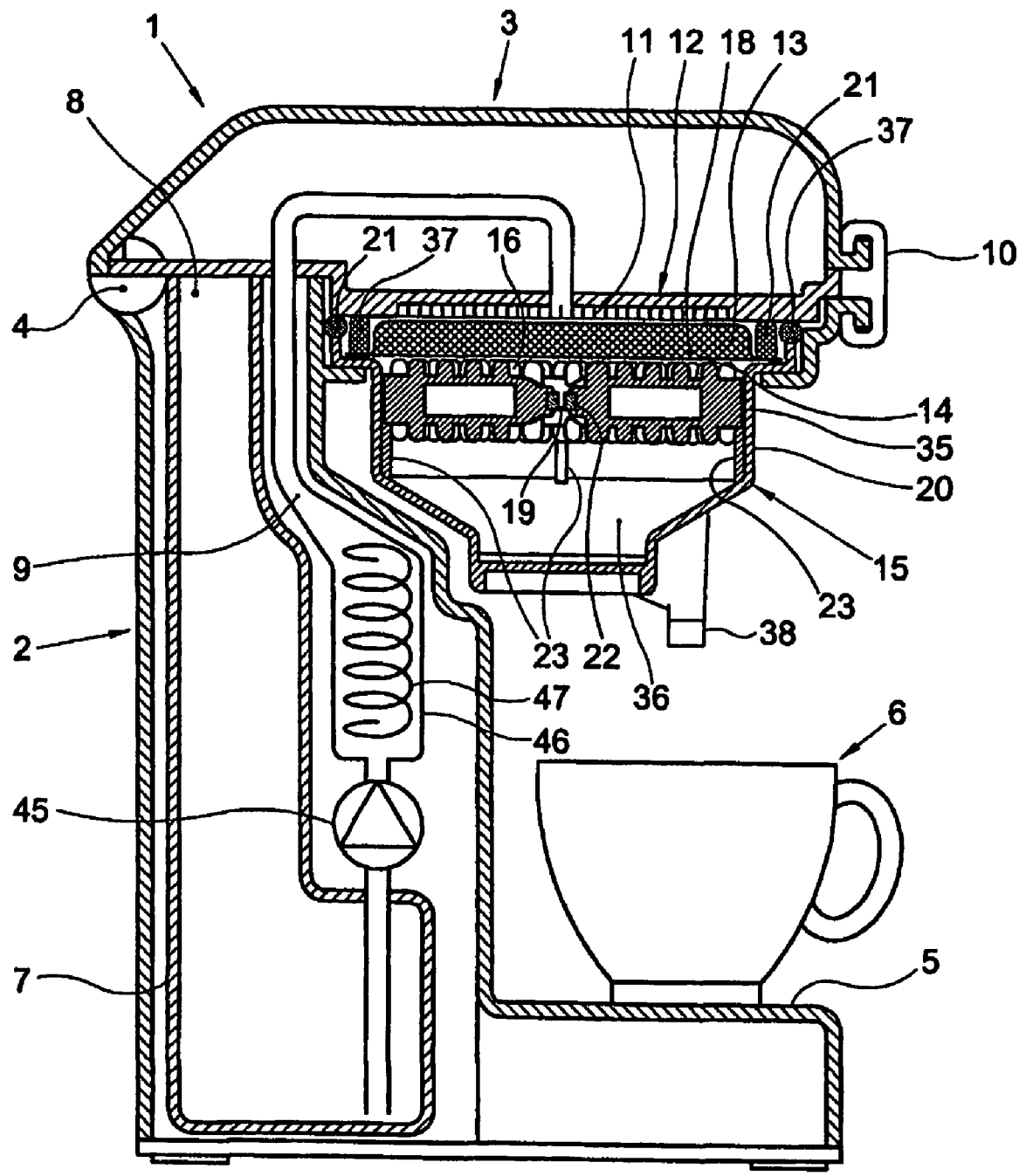
FIG. 1 is a cross-sectional view of an example of a coffee maker according to the present invention comprising an example of a brewing receptacle according to the present invention.
Figure 2:
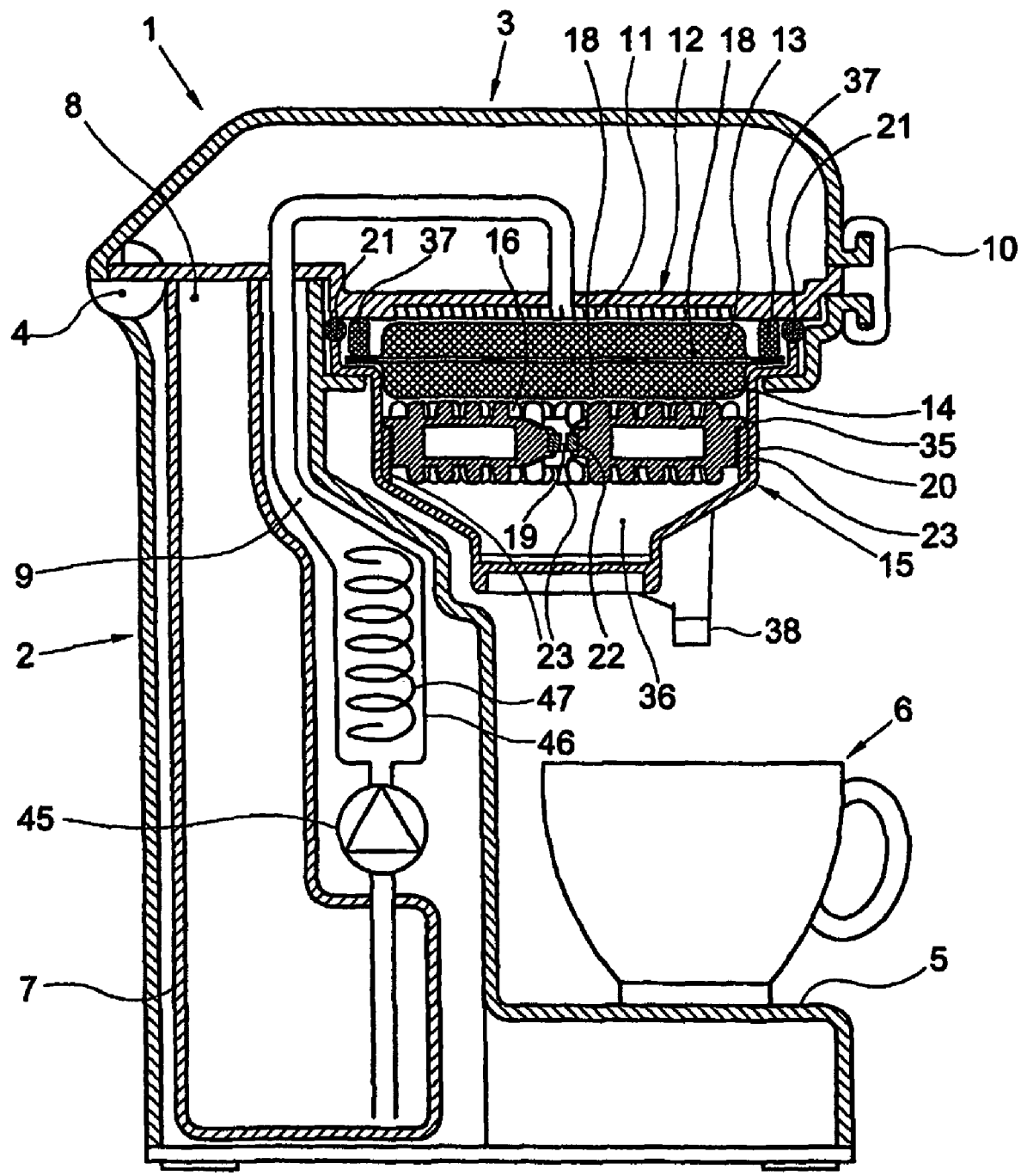
FIG. 2 is a cross-sectional view of the coffee maker of FIG. 1, but with the brewing receptacle in an alternative operating condition for accommodating more particles from which a beverage is to be brewed.

In FIGS. 1 and 2, reference numeral 1 designates a coffee maker according to the invention for preparing coffee extract having a small-bubble foam layer. In the present description of examples of embodiments of the invention, the product from which a beverage is to be brewed is a coffee granulate. It will be clear, however, that other products such as cocoa, milk powder, dried stock, tea, herbs, etc. may also be used as products from which beverages can be brewed.

The coffee maker 1 has a housing 2 and a cover 3 hinged to the housing 2 by a hinge 4 and fixed in closed position by a closure 10. The housing 2 has a forwardly extending portion of which a top surface 5 forms a plateau for supporting one or more cups 6 to be filled with coffee. Within the housing, a water reservoir 7 is located. A conduit 9 extends through a heating chamber 46 in which an electric heating element 47 is arranged. For providing a pressurized supply of water from the reservoir 8, a pump 45 is arranged in the conduit 9 upstream of the heater 47.

A sprinkling head 11 is integrated in a top wall 12 of a brewing chamber 13 in a brewing receptacle 15 and forms the end of the conduit 9. The brewing receptacle 15 has a bottom 14 forming the lower boundary of the coffee brewing chamber 13. Support stubs 16 of the bottom 14 project upwardly and interspaces between these projections 16 allow beverage liquid—coffee extract in the present example—pressed out of a pad or pouch 18 containing a ground coffee granulate or powder to flow to a discharge opening 19 in the bottom 14. The bottom 14 is supported by ribs 23 of a brewing receptacle housing part 20, which in turn is supported by portions of the main housing 2 of the coffee maker 1. In the operating condition, the brewing chamber 13 is watertightly sealed by seals 21, 35, and 37 so that no significant loss of pressure generated by the pump 45 occurs and all or virtually all pressure generated by the pump 45 is applied to the brewing chamber 13 when coffee is being extracted. If other drinks than coffee are to be prepared, the pad may contain other substances, for example cocoa powder and/or milk powder, which may be flavored and/or sweetened.

A nozzle 22 of which an upwardly oriented face forms part of the bottom 14 restricts the cross-section of the discharge opening 19 available for the passage of coffee extract. The nozzle 22 may also be an integral part of the pad support 15.

The discharge opening 19 debouches into a dispersing chamber 36 that communicates with two dispensing channels extending through dispensing spouts 38 via which coffee extract dispersed in the chamber can flow into the cups 6 on the platform 5. For forming foam on a coffee extract, the coffee extract is jetted from the nozzle 22 into a buffer quantity of coffee extract in the buffer reservoir 36.

The bottom 14 is invertible between a first operative position shown in FIG. 1 and a second operative position shown in FIG. 2. When the bottom 14 is in the first operative position, the brewing chamber 13 has a first volume for accommodating one coffee pad 18. When the bottom 14 is in the second operative position, the brewing chamber 13 has a second volume larger than first volume, for accommodating more particles, for instance in the form of a larger coffee pad or, as shown in FIG. 2, two coffee pads for preparing two cups of coffee or a stronger cup of coffee. According to the present example, the larger volume of the brewing chamber is adapted for receiving an amount of particles that is twice as large as the smaller amount of particles, so that the volumes are adapted for accommodating one and two pads or pouches, respectively, containing coffee granulate and/or other particles for preparing beverages.

The volume of the brewing chamber 13 can be changed in a simple manner by removing the bottom 14 of the brewing chamber 13 and remounting it in an inverted orientation.

According to the example shown in FIGS. 1 and 2, the bottom 14 rests essentially on top of the ribs 23 when the bottom 14 is in the orientation shown in FIG. 1. In the situation shown in FIG. 2, lateral slits in the bottom 14 receive upper portions of the ribs 23, which allows the bottom to sink to a lower position, which results in an accordingly enlarged volume of the brewing chamber 13.

Figure 3:
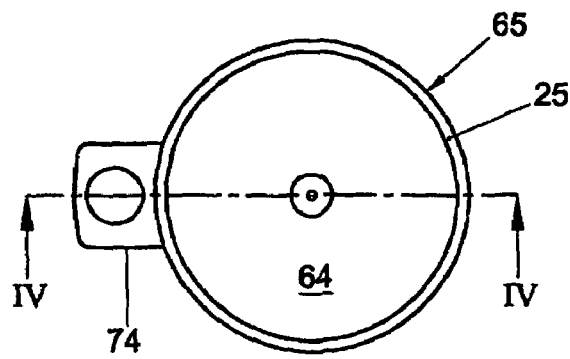
FIG. 3 is a top plan view of a second example of a brewing receptacle according to the invention.
Figure 4:
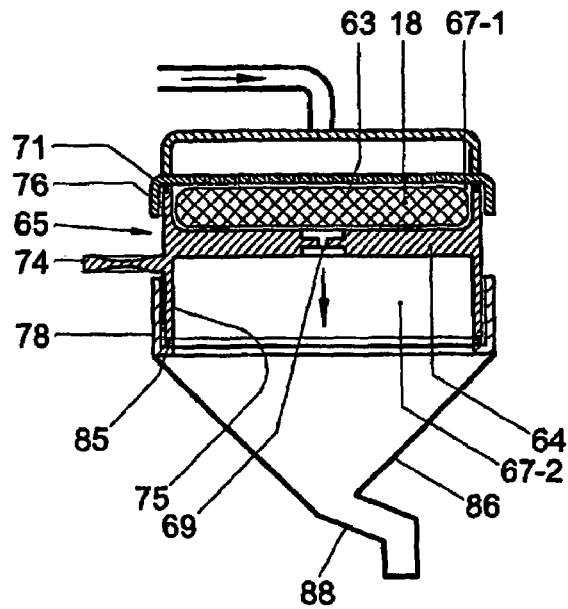
FIG. 4 is a lateral cross-sectional view taken on the line IV-IV in FIG. 3 of a brewing receptacle and of adjacent parts of a second beverage maker according to the invention.
Figure 5:
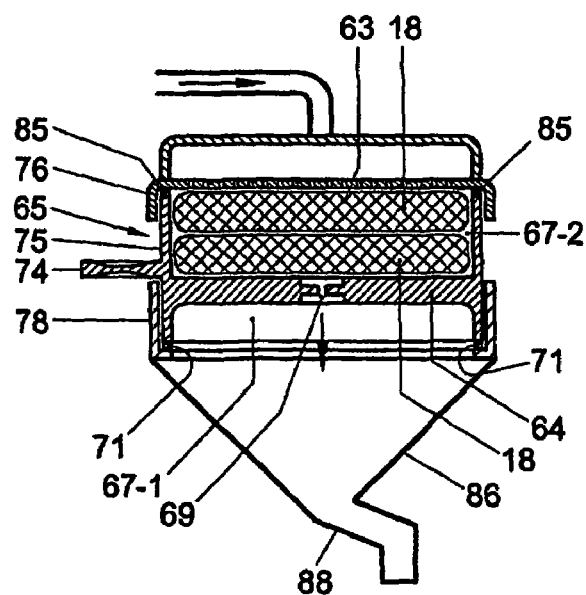
FIG. 5 is a view according to FIG. 4, but with the brewing receptacle in an alternative operating condition for accommodating more particles from which a beverage is to be brewed.

FIGS. 3 to 5 show an alternative, presently most preferred embodiment of a brewing receptacle according to the invention. According to this example, the brewing receptacle 65 comprises a first hollow 67-1 for receiving the particle pads 18 and a second hollow 67-2 for receiving the particles pads 18. The second hollow 67-2 has a larger volume than the first hollow 67-1, and the bottom 64 is located between the two hollows 67-1 and 67-2. The brewing receptacle according to this example allows changing of the volume of the brewing chamber 63 in that the whole receptacle 65 is dismounted and remounted in an inverted orientation. Since the bottom 64 is integrally connected to sidewalls 75 bounding the hollows 67-1 and 67-2, the receptacle has no separate bottom member and no seams between the bottom and the walls that would generally need to be sealed. The nozzle 69 through which coffee passes during brewing is located centrally in the bottom 64.

The receptacle 65 further comprises a handle 74 for manually holding the receptacle 65. The handle 74 is fixedly connected to and projects laterally from the bottom 64. Such a handle 74 is particularly suitable for manipulating the receptacle 65 between the two mutually inverted operating positions, because in both operating positions, the handle 74 can project from the receptacle 65 in the same direction where it can be easily reached by the user.

Furthermore, the handle 74 projects from a side wall 75 bounding the hollows 67-1 and 67-2, so that the handle does not project through a boundary of the brewing chamber 63, and an associated need to seal the handle against such a boundary is avoided.

According to the example shown in FIGS. 3 to 5, the beverage maker further comprises a receptacle fixture 76. In the operative condition shown in FIG. 4, a seal 71 is arranged for sealing a seam between an upper edge of the receptacle 65 and the receptacle fixture 76. In addition to the upper end of the receptacle 65, its lower end is also adapted for sealing engagement with the receptacle fixture 76, as can be seen in FIG. 5, where the end of the receptacle 65 that is lowermost in FIG. 4 now forms the upper end of the receptacle 65.

The beverage maker further comprises a beverage funnel 78. In the configuration shown in FIG. 4, a seal 85 seals a seam between the receptacle 65 and the beverage funnel 78. In the configuration shown in FIG. 5, the seal 85 seals a seam between the receptacle 65 and the receptacle fixture 76. A funnel-shaped beverage conduit 86 is arranged downstream of the beverage funnel 78 for guiding coffee to dispensing spouts 88.

Figure 6:
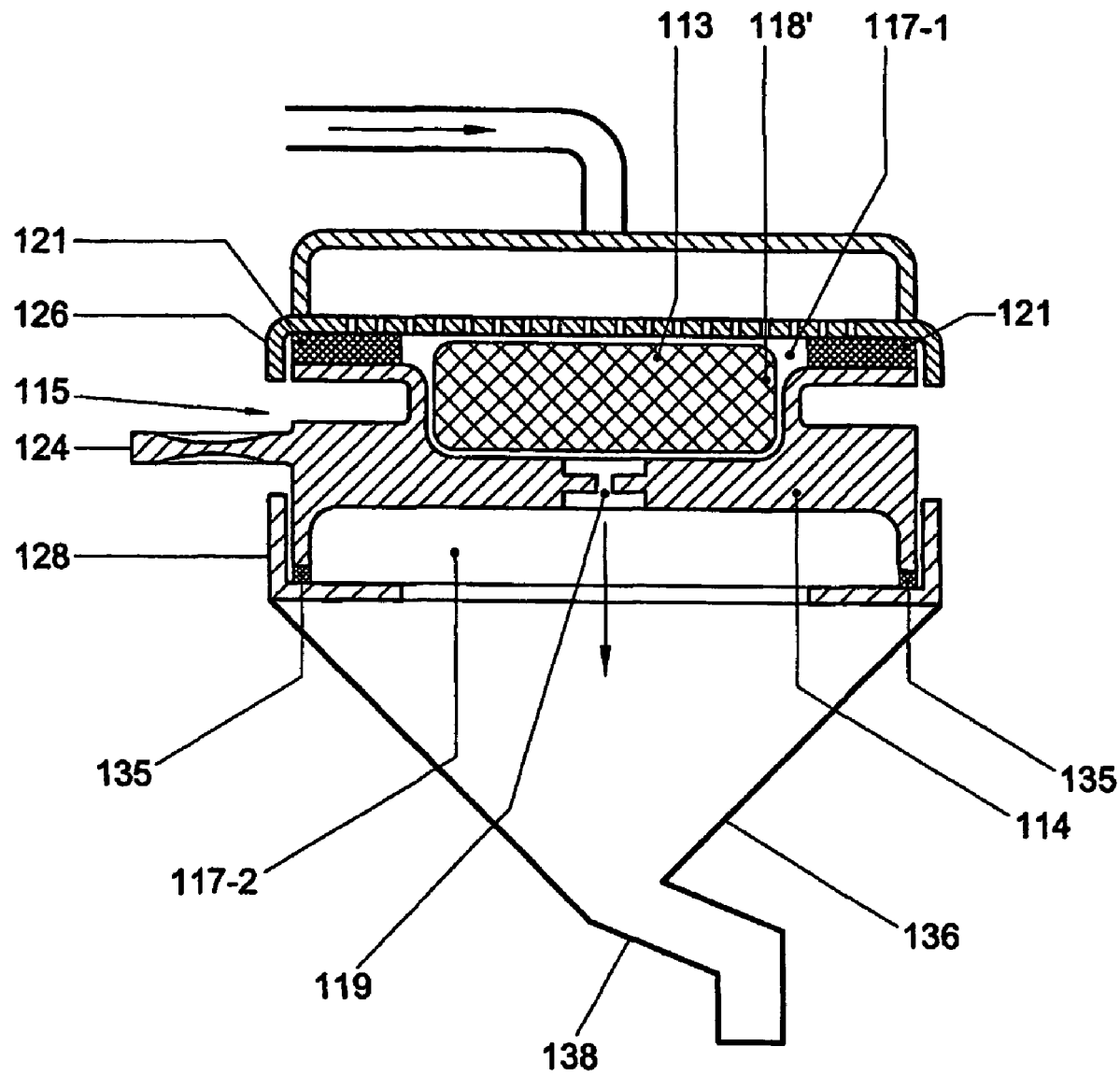
FIG. 6 is a lateral cross-sectional view of a third brewing receptacle according to the invention and of adjacent parts of a third beverage maker according to the invention.
Figure 7:
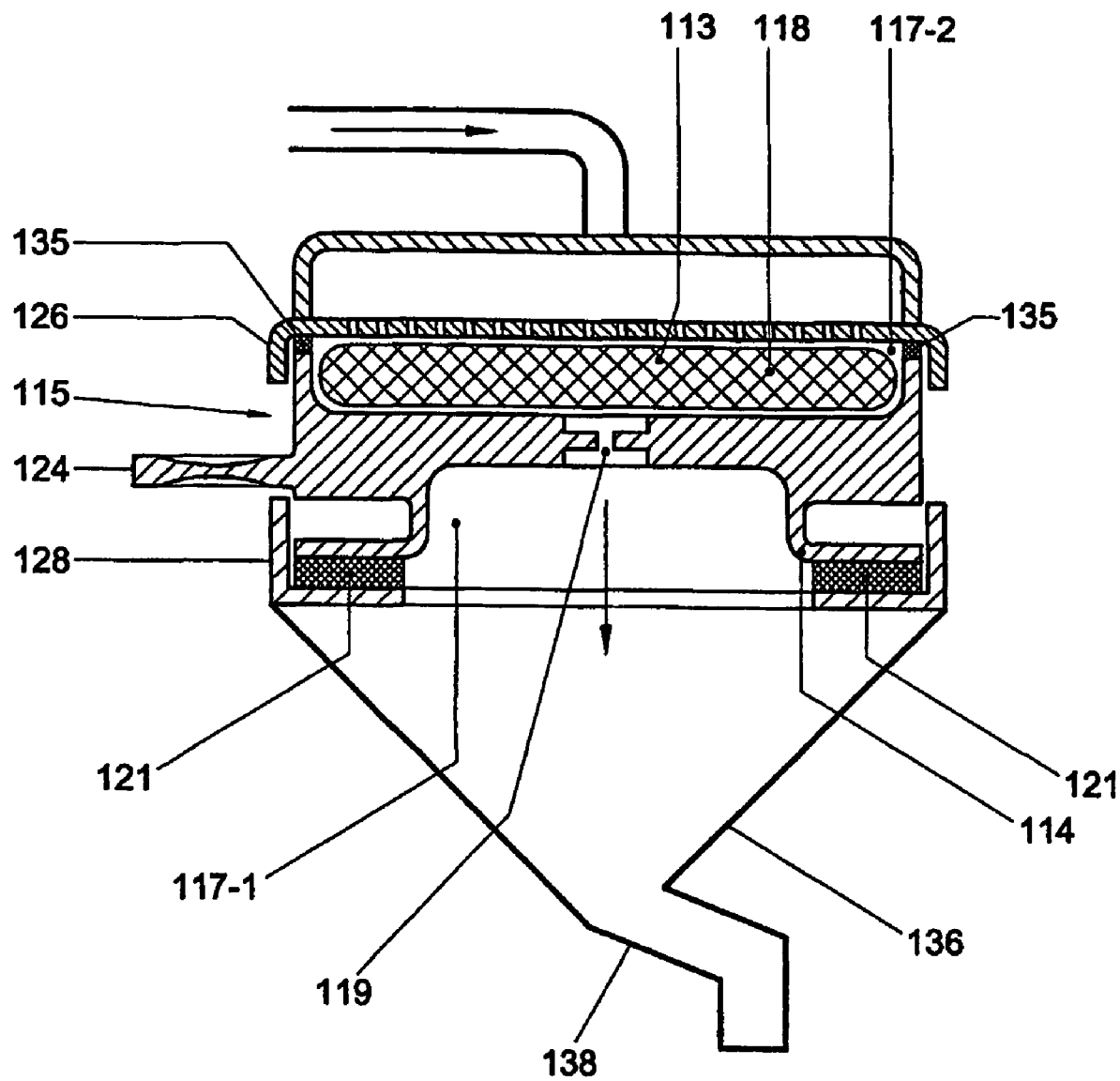
FIG. 7 is a view according to FIG. 6, but with the brewing receptacle in an alternative operating condition for accommodating the particles from which a beverage is to be brewed in another configuration.

FIGS. 6 and 7 show yet another alternative embodiment of a brewing receptacle according to the invention. According to this example, the brewing receptacle 115 comprises a first hollow 117-1 for receiving a particle pad 118' (or a plurality of particle pads of suitable size) and a second hollow 117-2 for receiving a particle pad 118 (or a plurality of particle pads of suitable size) having a larger cross-section transverse to the direction of passage of the water through the brewing chamber than the pad 118'.

Whereas, in the examples shown in FIGS. 1 to 5, inverting the bottom 14 of the operational brewing chamber 13 or inverting the whole receptacle 65 including its bottom 64 resulted in adapting the shape and the size of the brewing chamber 13 or 63 for accommodating different amounts of coffee (or other product for brewing a beverage), the differences between the hollows 117-1 and 117-2 are such that inverting the receptacle 115 including its bottom 114 results in changing the shape of the brewing chamber 113 while the volume remains essentially the same. This allows changing the shape of the operational brewing chamber between a relatively shallow shape having a large cross-sectional surface, in accordance with the shape of the second hollow 117-2 and a relatively deep shape having a smaller cross-sectional surface in accordance with the shape of the first hollow 117-1.

The relatively shallow shape of the brewing chamber 113 is particularly suitable for preparing coffee of low to medium strength and the relatively deep shape having a smaller cross-sectional surface is particularly suitable for preparing strong, i.e. very concentrated coffee. Thus, the brewing receptacle 115 according to this example allows changing the shape of the operational brewing chamber in accordance with the desired type of coffee to be brewed by dismounting the receptacle 115 and remounting it in an inverted orientation. The coffee granulate mixtures in the pads 118 and 118' may be different from each other, for instance with respect to fineness and type of coffee beans from which the granulate has been ground, and specifically adapted for preparing the respective types of coffee. Although, according to the present example, the volume of the brewing chamber 113 remains essentially the same if the receptacle 115 is inverted, it may be provided that the size and shapes of the hollows 117-1 and 117-2 are such that the volume also changes if the receptacle is inverted, for instance if the preferred amount of coffee for preparing one type of coffee is larger than the preferred amount of coffee for preparing another type of coffee.

In the operating condition shown in FIG. 6, a seal 121 is arranged for sealing off a seam between an upper edge of the receptacle 115 and the receptacle fixture 126. If the receptacle 115 is inverted, as is shown in FIG. 7, the seal 121 seals off a seam between the receptacle 115 and a beverage funnel 128. The seam between an upper edge of the receptacle 115 and the receptacle fixture 126 is then sealed by a seal 135, which seal seals off a seam between the receptacle 115 and a bezel 128 when the receptacle is in the orientation shown in FIG. 6.

The nozzle 119 through which coffee passes during brewing is located centrally in a lower portion of the bezel 128. During brewing, the coffee filtrate is jetted from the nozzle 119 into a foam unit 136 so that coffee with a foam ("crema") layer is obtained. The coffee is dispensed from a spout 138. Preferably arrangements are provided to maintain a temporary pool of coffee filtrate in a lower portion of the foam unit, into which the filtrate is jetted for enhancing foam formation.

If the first hollow 117-1 is facing upwards and towards the receptacle fixture 126, the outermost ones of the water supply channels in the sprinkling head are closed off by the seal 121. In the condition shown in FIG. 7, in which the large-diameter, second hollow 117-2 faces the sprinkling head 111, the outermost ones of the water supply channels are not closed off. For inverting the receptacle 115, it is provided with a grip 124 radially projecting from the receptacle 115.

Within the framework of the present invention, many embodiments other than those described above to illustrate the present invention are conceivable. For instance, it may be provided that the volume for receiving the product from which a beverage is to be brewed is variable by providing that a multiple brewing chamber is provided in at least one orientation of the receptacle or at least of the bottom, and the total volume of the operational brewing chamber or chambers is changed when the bottom or the whole receptacle is inverted. The receptacle may, for example, have one brewing chamber that is in a position operative for brewing a beverage when the receptacle or the bottom is in a first orientation and have two brewing chambers that are in a position operative for brewing a beverage when the receptacle or the bottom is in a second orientation inverted relative to the first orientation, so that the operative volume of the at least one brewing chamber is doubled if the receptacle or at least the bottom is inverted from the first orientation to the second orientation.

The invention claimed is:

1. A brewing receptacle comprising at least one brewing chamber operative for holding particles, the at least one chamber having at least one entry passage and an exit passage for displacing water through the chamber for brewing a beverage and having a bottom for supporting the particles and a discharge opening in said bottom for discharging beverage liquid through said bottom, characterized in that at least said bottom is invertible between a first and a second operative position, and in that the at least one operational brewing chamber has a first volume and a first shape when said bottom is in said first position and has a second volume and a second shape when said bottom is in said second position, at least one of said second volume and shape being different from said first volume and shape, respectively, the discharge opening being a nozzle.

2. A brewing receptacle according to claim 1, wherein said receptacle comprises at least one first hollow for receiving the particles and at least one second hollow for receiving the particles, wherein the at least one first hollow has a first volume and a first shape, wherein the at least one second hollow has a second volume and a second shape, and wherein at least one of said second volume and shape of said second hollow is different from said first volume and shape, respectively, of said first hollow.

3. A brewing receptacle according to claim 1, wherein said first volume is adapted for receiving a first amount of particles and wherein said second volume is adapted for receiving a second amount of particles, said second amount of particles being twice said first amount of particles.

4. A brewing receptacle according to claim 1, further comprising a handle for manually holding the receptacle, the handle being fixedly connected to and laterally projecting from said bottom.

5. A brewing receptacle according to claim 4, wherein the handle projects from a side wall bounding at least one of said hollows.

6. A set of parts including a brewing receptacle according to claim 1, at least a first pad containing a quantity of said particles and having a shape and dimensions in accordance with the shape and dimensions of said first brewing chamber for being accommodated in said first brewing chamber, and at least a second pad containing a quantity of said particles and having a shape and dimensions in accordance with the shape and dimensions of said second brewing chamber for being accommodated in said second brewing chamber, the shape and at least one dimension of said second pad being different from the shape and at least one corresponding dimension, respectively, of said first pad.

7. A foam unit comprising a brewing receptacle according to claim 1 and a buffer reservoir positioned downstream of the exit passage for retaining a buffer quantity of beverage liquid such that, in operation, beverage liquid is jetted from the exit passage into the buffer quantity of beverage liquid.

8. A beverage maker comprising:
   a water heating and feeding structure communicating with a brewing chamber for feeding hot water under pressure towards said brewing chamber;
   a brewing receptacle according to claim 1; and
   a beverage dispensing passage communicating with a buffer reservoir.

9. A beverage maker according to claim 8, further comprising a receptacle fixture adapted for sealingly engaging an upper edge of the receptacle, wherein the receptacle comprises a first hollow for receiving the particles and a second hollow for receiving the particles, wherein the second hollow has a larger volume than the first hollow, the bottom being located between the two hollows, and wherein the receptacle has an upper end and a lower end adapted for sealingly engaging said receptacle fixture.

* * * * *